United States Patent [19]

Weller et al.

[11] 4,456,684

[45] Jun. 26, 1984

[54] METHOD FOR SCREENING BACTERIA AND APPLICATION THEREOF FOR FIELD CONTROL OF DISEASES CAUSED BY GAEUMANNOMYCES GRAMINIS

[75] Inventors: David M. Weller; R. James Cook, both of Pullman, Wash.; Henry T. Wilkinson, Champaign, Ill.

[73] Assignee: The United States of America as represented by the Secretary of Agriculture, Washington, D.C.

[21] Appl. No.: 415,778

[22] Filed: Sep. 8, 1982

[51] Int. Cl.³ .......................... C12Q 1/20; C12N 1/00; C12R 1/39; C12R 1/645

[52] U.S. Cl. .................................... 435/34; 435/243; 435/253; 435/876; 435/911

[58] Field of Search ................. 435/34, 243, 245, 253, 435/254, 874, 876, 911

[56] References Cited

PUBLICATIONS

D. Hornby, "Take-all Decline: A Theorist's Paradise," *Soil-borne Plant Pathogens*, Ed. B. Schippers and W. Gams, Academic Press, New York, (1979), pp. 133–156.

P. J. Shipton, R. J. Cook, and J. W. Sitton, "Occurrence and Transfer of a Biological Factor in Soil that Suppresses Take-all of Wheat" in Eastern Washington, *Phytopathology*, vol. 63, No. 4, pp. 511–517, (1973).

R. J. Cook and A. D. Rovira, "The Role of Bacteria in the Biological Control of *Gaeumannomyces graminis* by Suppressive Soils," *Soil Biology and Biochemistry*, vol. 8, pp. 269–273, (1976).

G. B. Wildermuth, A. D. Rovira and J. H. Warcup, "Mechanism and Site of Suppression of *Gaeumannomyces graminis* var Tritici in Soil" *Soil-borne Plant Pathogens*, Ed. B. Schippers and W. Gams, Academic Press, New York, (1979).

M. E. Brown, Microbiology of Roots Infected with the Take-all Fungus (*Gaeumannomyces graminis* var Tritici) in Phased Sequences of Winter Wheat, *Soil Biology and Biochemistry*, vol. 13, pp. 285–291, (1981).

C. Eklund and C. E. Lankford, *Laboratory Manual for General Microbiology*, Prentice-Hall, Inc., Englewood Cliffs, New Jersey, (1967), pp. 21–27.

D. M. Weller and R. J. Cook, "Pseudomonads from Take-all Conducive and Suppressive Soils," *Phytopathology*, vol. 71, p. 264, (1981).

P. R. Merriman, R. D. Price and K. F. Baker, "The Effect of Inoculation of Seed with Antagonists of *Rhizoctonia soloni* on the Growth of Wheat," *Aust. J. Agric. Research*, vol. 25, pp. 213–218, (1974).

P. R. Merriman, R. D. Price, J. F. Kollmorgen, T. Piggott and E. H. Ridge, "Effect of Seed Inoculation with *Bactillus subtilis* and *Streptomyces griseus* on the Growth of Cereals and Carrots," *Aust. J. Agric. Res.*, vol. 25, pp. 219–226, (1974).

P. Broadbent, K. F. Baker and Y. Waterworth, "Bacteria and Actinomycetes Antagonistic to Fungal Root Pathogens in Australian Soils," *Aust. J. Biol. Sci.*, vol. 24, pp. 925–944, (1971).

E. M. Reis, R. J. Cook and B. L. McNeal, "Effect of Mineral Nutrition on Take-all of Wheat," *Phytopathology*, vol. 72, p. 225, (1982).

Weller et al., Suppression of Take-All of Wheat by Seed Treatment with Fluorescent Pseudomonads, Phyto. Soc., vol. 73 (#3), 1983.

Weller et al., Control of Take-All with Flourescent Pseudomonads, Phyto., vol. 71 (#9), 1981.

Vrany et al., Control of Micro. in Rhizosphere of Wheat by Innoculation of Seeds with *Pseudomonas putida* and by Foliar Application of Urea, Instit. of Micro., 1979.

*Primary Examiner*—Robert A. Yoncoskie
*Assistant Examiner*—Marianne S. Minnick
*Attorney, Agent, or Firm*—M. Howard Silverstein; David G. McConnell; Margaret A. Connor

[57] ABSTRACT

A method for screening bacteria to select strains which will suppress diseases caused by the fungus *Gaeumannomyces graminis* (Gg) under field conditions and a method for applying field-suppressive bacteria to suppress Gg in a commercial setting. Four fluorescens Pseudomonas strains are disclosed which are effective in suppressing take-all in wheat.

25 Claims, No Drawings

METHOD FOR SCREENING BACTERIA AND APPLICATION THEREOF FOR FIELD CONTROL OF DISEASES CAUSED BY *GAEUMANNOMYCES GRAMINIS*

BACKGROUND OF THE INVENTION

This invention relates to and has among its objects the isolation, selection, and application of bacteria to control in the field diseases caused by *Gaeumannomyces graminis* in plants, such as take-all in wheat and Ophiobolus patch in turf grass. Further objects of the invention will be evident from the following description wherein in parts and percentages are by weight unless otherwise specified.

Widespread diseases of cereal crops and turf grass are caused by the soil-borne fungus *Gaeumannomyces graminis* (Gg) and result in significant economic loss due to reduction in crop yield. Take-all, a disease caused by *Gaeumannomyces graminis var tritici* (Ggt) is a severe disease of wheat. Ggt also infects other cereal crops such as barley, rye, and oats as well as wild and cultivated grasses. Symptoms of wheat take-all include dark longitudinal lesions on roots; in severe cases, the entire root may become blackened with disease with the fungus migrating to the crown of the wheat plant (where the crown roots originate) and the tillers (stems). Severely infected wheat plants are identified in the field by their white heads which result when infection of the crown by the fungus cuts off water transport to upper plant parts causing the plant to die prematurely. It has been estimated that in the Pacific Northwest (Washington, Oreg., and Idaho), an area where wheat is the fourth most important irrigated crop, take-all commonly causes a 5-20 percent reduction in the yield of wheat. On a world-wide basis, take-all is the most important root disease of wheat, causing reduction in yield in fields where wheat has been grown two or more years in succession.

Another Gg fungus, *Gaeumannomyces graminis var. avenae* (Gga), infects oats and grasses and has been identified as causing Ophiobolus patch in turf grasses such as bent grass and the like. *Gaeumannomyces graminis var graminis* (Ggg) infects some grasses and has been suggested as causing Brown Sheath Rot in rice.

Control of Gg-caused disease is important to prevent crop losses and maintain healthy turf grass. Presently, however, control of wheat take-all by fungicides is considered economically impractical and Gg-resistant cereal or grass varieties are not known in spite of searches over the past 50 years.

Some natural suppression of Ggt has been found to occur in certain circumstances. For example, take-all decline (TAD), a natural suppression of take-all, develops in soils where Ggt-susceptible cereals have been grown in monoculture for many years. TAD has been extensively studied in an attempt to determine what conditions are responsible for natural suppression. Theories put forward to explain this phenomenon include changes in the microbiological status of the soil, build-up of antagonistic bacteria, changes in the pathogenicity and population of the fungus, concentration and form of nitrogen in the soil, presence of protective fungi and presence of volatile substances such as ethylene in the soil, D. Hornby in "Take-All Decline: A Theorist's Paradise," *Soil-borne Plant Pathogens*, Ed. B. Schippers and W. Gams, Academic Press, New York (1979) pp 133-156. Hornby reviewed these explanations and concluded that no single hypothesis could explain take-all decline and that opposing views may be concerned with various facets of the same complex phenomenon.

Investigators have carried out two types of studies to assess microbial antagonism in the suppression of Ggt. One type of study involves the transfer of suppressiveness by incorporating a small amount of monoculture wheat-field soil into a take-all conducive soil. This procedure has had only partial success. For example, when fumigated soil containing added Ggt-inoculum was amended with one percent take-all suppressive soil, restoration of antagonistic properties was provided in the greenhouse; however, the same treatment in field plots resulted in only a dealy of take-all in the first year and suppression in the second year. Plots amended with soil from take-all conducive virgin (uncropped) sites did not show take-all suppression until the third year thus demonstrating the difference in antagonism between cropped and virgin soils, and the transmissibility of a biological factor antagonistic to Ggt in the greenhouse and the field (P. J. Shipton et al., Phytopathology, Volume 63, pp 511-517 (1973) (Shipton et al.)). In a similar study, 10 percent of a take-all suppressive soil from a field cropped 21 consecutive years to wheat and a take-all conducive soil were added to fumigated soil, the mixtures amended with one percent Ggt-inoculum and planted to wheat. After two successively croppings, plants grown in the suppressive soil showed suppression of take-all, while plants grown in the conducive soil were not protected. The roots of plants grown in the suppressive soil had higher numbers of pseudomonads than plants grown in the conducive soil, (Weller and Cook, Phytopathology, Volume 71, p. 264 (1981)). These studies indicate that although suppressiveness can be transferred, suppression of take-all does not occur in the field until after the first or second crop year. In addition to not being completely successful, the method of incorporation of monoculture soil to suppress take-all is impractical on a commercial basis as it requires the transfer of tons of soil to the field plots.

The second type of study of microbial antagonism involves the attempt to identify specific Ggt-antagonistic microorganisms and transfer these organisms to soil to reproduce suppression. Studies of specific Ggt-antagonistic microflora which developed in TAD showed that actinomycetes, fungi, and bacteria, especially Pseudomonas spp., were found prominent at times (Hornby, p. 151). However, not all organisms present in take-all suppressive soil were found to suppress take-all. In field trials, only one percent of bacteria isolated from TAD soil and added back to take-all conducive soil effectively antagonized Ggt (Hornby, p. 142). Shipton et al. developed a pot assay to assess take-all suppression by specific microorganisms in the greenhouse. Using this test, Cook and Rovira (Soil Biology and Biochemistry, Volume 8, pp. 269-273, 1976) (Cook and Rovira) took candidate isolates of bacteria and actimomyces from soil, and from diseased and protected wheat roots and tested them as soil treatments to suppress Ggt. Pure cultures of each isolate were grown for 1-2 days in sterile soil and then this "soil inoculum" was mixed with potting soil (1 g soil inoculum per 100 g potting soil). The soil mixture was infested with the take-all fungus (0.1 to 0.5 percent (w/w) Ggt. oat-kernel per soil mixture) and planted to wheat. Of the isolates tested only eight cultures suppressed take-all in the greenhouse. These were identified as Pseudomonas spp.

(seven were fluoroescent). While this work identified bacteria present in TAD soil which could impart suppression to wheat seedlings planted in potting soil in the greenhouse, no practical treatment for control of take-all in the field was demonstrated or suggested by the researchers. An equivalent field treatment by the above method of Cook and Rovira would require about 10 tons of the soil inoculum per acre mixed 6 inches deep.

Another complication in finding a biological control of Ggt was that other experiments, namely, cereal sequence experiments taught away from the use of fluorescent pseudomonads to suppress take-all. These studies indicated that fluorescent pseudomonads were often only a small fraction of the total bacterial antagonists which inhibit Ggt and play little or no role in natural suppression of take-all associated with take-all decline. (Soil Biology and Biochemistry, Volume 13, pp 285-291 (1981) (Brown)). Thus, although some information about the influence of soil microflora on TAD existed, the problem remained of how to screen microorganisms for antagonism to Gg-fungus, to select those which would provide disease suppression under field conditions and to find a practical method of field application. This step from successful antagonism in the greenhouse to success in the field is difficult to achieve because in the greenhouse, conditions such as soil temperature, soil moisture, other plant disease, and the like are controlled whereas in the field, presence of other disease and microorganisms in the soil, cultivation and soil temperature and soil moisture vary considerably throughout the growing season.

Furthermore once a field-effective bacteria was selected, the problem of an economical and practical method of applying the bacteria in a commercial setting remained to be found.

SUMMARY OF THE INVENTION

We have discovered a novel method for screening bacteria for selection of bacterial strains which will suppress (reduce the incidence or severity of) diseases caused by the fungus Gaeumannomyces graminis (Gg) under field conditions and a practical and effective method for applying Gg-suppressive bacteria in the field to suppress Gg in Gg-susceptible crops or grasses in a commercial setting. We have also discovered four strains of Pseudomonas fluorescens which are effective in suppressing Gaeumannomyces graminis var. tritici (Ggt) in field-grown crops and turf grass.

The screening method comprises:

1. Isolating strains of potentially suppressive bacteria—that is, bacteria having the potential for suppressing Gg—from roots of the variety of plant to be protected which have been grown in soil amended with Gg-fungus;

2. Subjecting the so-isolated bacteria of step 1 to a first screening in the greenhouse as follows: growing plants of the variety to be protected in the greenhouse in the presence of the bacteria and in the presence of Gg-inoculum having a particle size and concentration such that the bacteria is subjected to an inoculum pressure which maximizes the selection of the number of strains which have the potential to suppress Gg in the field and minimizes the selection of field-ineffective strains; growing control plants as above but without the addition of bacteria and selecting those bacteria which cause bacterial-treated plants to exhibit certain defined criteria such as greater height, greater weight or less root disease than the control plants.

3. Subjecting bacteria which suppress Gg in the greenhouse to a second screening under field conditions as follows: growing in the field plants of the variety to be protected in the presence of bacteria screened in step 2 and in the presence of Gg-inoculum in a particular concentration such that the bacteria is subjected to an inoculum pressure which maximizes the selection of the number of strains which have the potential to suppress Gg in the field and minimizes the selection of field-ineffective strains; growing control plants in close proximity to the bacterial-treated plants; and selecting those strains of bacteria which cause plants to exhibit certain defined criteria such as greater height or less root disease than control plants (plants grown in infested soil without added bacteria.)

Our application procedure to biologically control Gg-caused disease in a commercial setting comprises adding a suppressive amount of Gg-suppressive bacteria to seeds prior to planting or applying a drench containing a suppressive amount bacteria to growing plants. The former method is the only practical method for controlling Gg in small grain cereal crops such as wheat, rye, oats, barley and the like grown in large commercial fields; the latter method of application is particularly suitable for controlling Gg fungus in short stands of plants such as turf grass.

Objects of this invention are the provision of a means for screening bacteria for strains which suppress disease-causing Gg fungus under field conditions and a means for applying Gg-suppressive bacteria so as to control disease in the field. The need for a biological control of Gg fungus has long been sensed as crop losses due to the disease have been significant and control by fungicides impractical. Furthermore, no Gg-resistant cereal or grass varieties are presently known. By using the particular procedures and conditions of our screening method, strains of bacteria can be selected which will suppress Gg fungus in the field. By using our application method, Gg-caused disease can be controlled in a commercial setting.

Prior to our method, both in vitro and in vivo tests had been tried to assess field-effectiveness. None were completely successful, in vitro tests, that is, tests of bacteria using standard laboratory bacterial procedures, were ineffective as no single or combination of physiological or morphological characters of the strains in vitro were shown to predict field-effective strains. For example, although 80 percent of random strains of Pseudomonas fluorescens isolated from wheat roots exhibit at least some antibiotic effect against the take-all fungus in vitro, most of the isolates gave no biocontrol as a seed treatment in vivo, that is, on living plants. In in vivo testing, although the in vivo tests of Cook and Rovira identified Ggt-antagonistic bacteria in soils exhibiting natural suppression, such isolates were never shown as capable of controlling Ggt in the field, and no method of screening for field-effectiveness or application for commercial use was disclosed or suggested. As stated previously the step from suppression in the greenhouse to control in the field is difficult to achieve due to lack of control in the field of such variables as soil conditions, soil moisture and temperature, plant disease and the like. By use of the instant invention, however, it is possible to assess bacteria for field effectiveness and to apply Gg-suppressive bacteria for control of disease causing Gg-fungus such as take-all in wheat, Ophiobolus patch in turf grass and the like.

DESCRIPTION OF THE PREFERRED EMBODIMENTS

Step 1. Isolation of Strains of Potentially Suppressive Bacteria

The bacteria to be isolated must have the ability to establish and grow in the microhabitat where it is to be used to suppress Gg-disease causing fungus. The standard procedure is as follows:

First, the soil in which the bacteria are to be grown is amended with Gg fungus. The preferred method is to amend the soil with about 0.1 to 1.0 percent (w/w) Gg inoculum per total soil. Inoculum can be prepared using any grain, however oat grains are the preferred medium. Other methods known in the art can be used to amend the soil such as amendment of the soil with plant roots infected with Gg fungus or dilution of the soil with a fumigated soil (1:10(w/w)) followed by amendment with 0.1 to 1.0 percent (w/w) Gg-colonized oats or the like.

Next, plants of the variety to be protected from disease-causing Gg fungus are propagated in the amended soil. For example, where it is desired to isolate bacteria having the potential for suppressing wheat take-all in the field, wheat seeds are planted in the amended soil. The seeds are allowed to germinate and the plants grow for a time and at a temperature suitable for propagating the potentially suppressive bacteria, generally, 4 to 8 weeks at about 10° to 20° C.

The bacteria are then collected as follows: The propagated plants are gently removed from the soil and excess soil removed from the roots by shaking. The roots with lesions along with adhering soil (rhizosphere soil) are macerated in a mortar and pestle with water or suitable buffer such as 0.01M phosphate buffer. Serial dilutions of the homogenate are prepared and plated onto a culture medium by standard techniques such as described in Eklund and Lankford, Laboratory Manual for General Microbiology, Prentice-hall, Inc., Englewood Cliffs, N.J. (1967), pp. 21–27. Next the bacteria are incubated for 2 to 5 days at a temperature suitable for bacterial growth, generally about 20° to 27° C. The bacteria may be grown on a general medium or a medium selective to one group of bacteria. Examples of general media which propagate a broad number of bacteria include nutrient broth yeast extract agar (NBY), nutrient agar and the like. An example of a selective media is King's medium 'B', (KMB) amended with the antibiotics novobiocin, penicillin and cycloheximide which is used to detect pseudomonads.

Individual strains (colonies) of the so-propagated bacteria from the previous step are individually streaked onto a media suitable for bacterial growth and selected and restreaked until each selected strain is pure and stable. Each strain is maintained to keep it stable such as by storing on a slant at low temperature, (about 5° C.), storing in an aqueous solution of glycerol at −10° C. or lyophilizing and storing at −10° C.

Step 2. Screening of the Bacteria in the Greenhouse

Bacterial strains isolated in the previous step are subjected to a first screening under greenhouse conditions using Gg inoculum of a particular particle size and concentration which present the bacteria with an inoculum pressure so as to maximize the number of suppressive bacteria which have potential for working under field conditions.

In this test, plastic, conical-shaped tubes (cones) are used as small, slender pots. A 15-cm long cone has been found to be a convenient size for the greenhouse work with 1–2 seeds or 1 cm diameter plug of grass planted in each cone. The cone is first filled about half full with a material such as vermiculite which functions to support the soil. Next, Gg-inoculated soil is added to the cone.

Inoculation of the soil is carried out as follows: Gg fungus to which suppression is desired is added to the soil as an inoculum prepared according to the procedure of Reis et al., Phytopathology, Volume 72, p. 225 (1982). The inoculum is pulverized and seived and the particles mixed with soil at a particular concentration. The effective ranges of inoculum concentration and particle size are those which optimize the selection of field-effective strains and minimize the selection of field-ineffective strains. The concentration of inoculum must be high enough so that sufficient inoculum pressure is placed on the bacterial strain being tested and strains having little or no suppressive activity are not selected; conversely, the concentration of inoculum must be low enough so that it does not overpower the suppressive activity of the bacterial strain such that field-effective strains are not selected.

Choice of particle size is determined by similar criteria. The particle size of the inoculum must be large enough so that the bacterial strain is presented with inoculum pressure sufficient to screen out strains having little or no suppressive activity; the inoculum size must not be so great that the inoculum over powers the strains and field-effective strains are not selected.

Selection of concentration and size of Gg fungus inoculum depends on the virulence of the Gg fungus, strength of the inoculum and conduciveness of the soil to the Gg fungus. In the greenhouse test for cereals, the preferred inoculum concentration range is about 0.05 to 1.0 percent inoculum per total weight of soil; the more preferred range is about 0.15 to 0.45 percent. In the greenhouse test for turf grass, the preferred inoculum concentration range is about 0.5 to 4.0 percent inoculum per total weight of soil; the more preferred range is about 1 to 3 percent. Concentration at either or both ends of the ranges or intermediate concentrations can be used in the greenhouse test. The preferred range of particle size is about 0.25 to 1 mm. Generally smaller ranges of particle size are used such as from about 0.25 to 0.5 mm or about 0.5 to 1 mm. However, either size range or any combination thereof is encompassed by the invention.

Bacteria of the strain isolated in step 1 are mixed into an aqueous solution of methylcellulose or comparable sticking agent, said methylcellulose being present in a concentration sufficient to minimize dessication of the bacteria and cause it to adhere to the seed or soil, generally about 0.5 to 2 percent in water. The bacteria-methylcellulose solution is then either added directly to the seeds, incorporated into the soil, or drenched onto the turf grass. The concentration of bacteria used as a soil treatment in the greenhouse test for suppression of Gg in cereals is about $1 \times 10^6$ to $1 \times 10^7$ bacteria per gram of soil; for turf grass, 2 ml of a drench containing about $1 \times 10^7$ to $1 \times 10^9$ bacteria per ml is added to a 1-cm diameter plug of grass.

The seed treatment is as follows: first, seeds are surface sterilized by immersing in a 2.6 percent solution of sodium hypochlorite (a 50 percent solution of bleach) for 3 minutes, then rinsed under a continuous stream of distilled water for at least 3 minutes, and dried overnight under an air stream. Bacterial strains produced as described in step 1 are added to a suspension containing 0.5 to 2 percent of a sticky, suspending agent such as methylcellulose in water. The seeds are added to the suspension and thoroughly mixed so that each seed is coated with about $1 \times 10^7$ to $2 \times 10^8$ bacteria per seed. The amount of bacteria per seed is varied within the above range depending on whether or not the soil is fumigated (fumigated soil is highly conducive to disease compared to natural soil.) In general, the preferred amount is about $1 \times 10^8$ bacteria per seed. After addition of the seeds or turf grass plug to the cones, vermiculite is added. Thus, the soil containing the Gg fungus and through which the roots must grow is sandwiched as a layer between two layers of vermiculite. Vermiculite is a preferred rooting medium in the greenhouse because of its good drainage characteristics—similar to that encountered by roots in the field, however other rooting media may be used.

Next the cones containing bacterial-treated seed, soil, or soil drench are moistened with water which moves as a wetting front downward through the vermiculite and soil; the cones are incubated using a dark/light cycle of 12 hours. After about 3 to 4 weeks for cereals and 6 to 8 weeks for turf grass, the seedlings are pulled up, washed with water and evaluated for size and number of root lesions or amount of dry weight against controls which are grown as above except that bacteria is not added. Strains which pass the criteria outlined below are tested in the field and ineffective strains discarded. To have statistical significance, a minimum of 3 cones per treatment must be used.

Evaluation of Seedlings in Greenhouse Test:

Cereals: Wheat, barley, rye or oat seedlings treated with Gg-suppressive strains of bacteria have fewer root lesions and are taller than untreated plants grown in soil infested with the fungus. To evaluate bacterial treatment, the plants are measured from the base of the stem to the tip of the largest leaf. Root disease is rated on a 0-5 scale: 0=no disease, 1=one or two lesions on the roots of a given plant, 2=50-100 percent of the roots of the plant with one or more lesions each, 3=all roots of the plant with lesions and some evidence of infection of the stem, 4=lesions abundant and beginning to coalesce on the stem, and 5=plant dead or nearly so. In order for a bacterial strain to be considered suppressive, the seedlings treated with bacteria of the strain must after 3 to 4 weeks growth at 10° to 20° C. and preferably 15° to 18° C. average at least 0.3 cm taller or average at least 0.5 units less root disease (rating scale 0–5) than comparable untreated but diseased seedlings. The preferred evaluation procedures in the greenhouse is the root disease rating method.

Grasses: Grass treated with Gg-suppressive strains of bacteria have a thicker root system and foilage than untreated plants grown in soil infested with the fungus. To evaluate bacterial treatments, the dry weights of the washed root system or the foilage are determined. In order for the bacterium to be considered suppressive, the grass treated with the bacteria must after 6 to 8 weeks growth at 10° to 20° C. average at least 5 percent greater root or foliage dry weight than comparable untreated grass.

Step 3. Screening the Bacterial Strains in the Field

Cereals: Bacterial strains which suppress Gg in cereal seedlings growth in infested soil in the greenhouse in the previous step are next tested in the field as follows: Plots are laid out in a manner suitable for statistical evaluation such as a randomized block design or latin square. Treatment plots consisting of three or four 3-meter rows are preferred. The control (non-treatment) plot should be within close proximity to the comparable treatment plot rather than distributed randomly within the block so that treatment and non-treatment plots have similar soil conditions, soil moisture and the like. Where three or four 3-meter rows are used, the control plot should be within about three meters of the treatment plot.

Planting is as follows: Seed furrows are opened to about a 10-cm depth using a V-shaped cultivator. Gg inoculum is added to the furrow. The effective range of concentration of inoculum is that which optimizes the selection of field-effective strains and minimizes the selection of field-ineffective strains. The preferred concentration is about 4 to 5 g of inoculum per 3-meter row; the more preferred concentration is 4.5 g per 3-meter row. It is preferred that the inoculum comprise whole kernels as this size readily distributes uniformly under field wind and weather conditions. Seed which has been coated with bacteria as described previously (treatment plot) is added to the furrow so as to provide a uniform stand of crop sufficient to assess the treatment, preferably about 150 to 250 and preferably 200 plants per 3-meter row (approximately 7 to 7.5 g of seed per 3-meter row). Control plots are the same as above except that the seed is not coated with bacteria.

Evaluation of cereals in the field test:

To assess the effect of bacterial seed treatment on the control of Gg-fungus in cereals grown in the field, various measurements are taken at intervals throughout the growing season and at maturity. The measurements include counting the number of plants with severe foliage symptoms (plants with one or more flacid, yellow leaves); measuring plant height; counting the number of heads per row; counting the number of dead tillers (white heads); determining the amount of root infection; and determining yield.

Cereal plants grown in soil infested with a Gg pathogen such as take-all but treated with a Gg-suppressive bacterial strain are taller, have more heads, yield more, or have less root disease compared to untreated, unprotected plants. The plants are measured before the heading state; heads are counted during the dough stage; and roots are rated during the jointing stage. Root disease is assessed on a 0–5 scale: 0=no disease, 1=less than 25 percent of the roots black, 2=25 to 100 percent of the roots black, 3=lesions at the base of the tillers, 4=lesions moving up the tillers and 5=plants severely stunted or dead. In order for a bacterial strain to be considered suppressive to take-all, the plants treated with a bacterial strain must average at least 1 cm taller, 5 percent more head, 5 percent greater yield or 0.1 units less root disease than comparable untreated but take-all infected plants. The preferred evaluation procedure in the field is height measurement or head count.

Grasses: Bacterial Strains which suppress Gg in grass seedlings grown in infested soil in the greenhouse in the previous step are tested in the field as follows: Plots are laid out in an established lawn of grass in a manner suitable for statistical evaluation with control (non-treatment) plots adjacent to treatment plots. At least three replicates for each are planted. The preferred plot size is a one meter$^2$ patch. The effective range of concentration of inoculum is that which optimizes the selection of field-effective strains and minimizes the selection of field-ineffective strains. Preferably 9 to 11 and more preferably 10 grams of whole or pulverized oat-kernel inoculum are added per square meter of grass.

An aqueous suspension of $1 \times 10^7$ to $1 \times 10^9$ test bacteria per ml in about 0.5 to 2 percent methylcellulose is prepared as a soil drench. The drench is added at a concentration of about 1 liter per square meter of grass and watered into the crown area of the grass. Alternatively, the bacterial treatment can be applied directly to the soil before seeding or sodding.

Evaluation of grasses in the field test:

A patch of grass grown in soil infested with a Gg pathogen such as Gga but treated with a Gg-suppressive bacterial strain is greener and has less areas of dead grass compared to untreated, unprotected patches of grass. Disease is assessed by measuring the area of the patch that is yellowed, measuring the rate at which the edges of the yellowed area continue to expand outward and measuring the dry weights of the root systems or foliage (cut grass). In order for a bacterial strain to be considered suppressive to Gg, the treated grass must average at least 5 percent less yellowed area or 5 percent more root or foliage dry weight than comparable untreated grass. Method of Application of Gg-suppressive Bacteria for control of Gg-caused disease in a commercial field.

Method of Application of Gg-suppressive Bacterium for Control of Gg-caused Disease in a Commercial Field One of two methods are used to control Gg in a commercial setting depending on whether the field is planted with seed or comprises a standing crop. For small grain cereal crops such as wheat, oats, rye, barley and the like, which are grown from seed, the bacteria must be applied to the seed in a Gg-suppressive amount, that is, an amount sufficient to suppress Gg fungus in the field. The seed is then planted. For turf grass, where a lawn of grass exists, a drench containing a suppressive amount of bacteria is applied to the grass.

Cereals: Individual strains of bacteria which suppressed Gg in the greenhouse and field tests or other biologically pure strains of bacteria shown to suppress Gg fungus in the field are cultured by standard methods for about 48 hours prior to treatment to achieve sufficient bacteria to treat the seeds. The bacteria are scraped into an aqueous suspension of about 0.5 to 2 percent methylcellulose and preferably 1 to 1.5 percent methylcellulose. The seeds to be treated are added to the suspension and thoroughly mixed so that each seed is coated with about $1\times10^7$ to $2\times10^8$ and preferably $1\times10^8$ bacteria per seed. The seeds are dried and clumps of seeds are broken up so that they can be sown using a commercial seeder such as a grain drill.

Treated seeds are sown by conventional means such as a grain drill with disk or hoe row openers. By use of the above method, increased yields resulting from disease control can be obtained with wheat grown in a commercial field containing take-all fungus.

Turf grass: To suppress the Gg-fungus in an infected patch of turf grass or the like where a stand of grass exists, the bacterial strain is cultured as described above. Next, the bacteria are scraped into a 0.5 to 2 percent and preferably 1 to 1.5 percent suspension of methylcellulose (or comparable sticking agent) and the concentration is adjusted to between $1\times10^7$ and $1\times10^9$ bacteria of the strain per ml. Each 1 $m^2$ area of a lawn is treated with about 1 liter of the bacterial treatment. The bacteria can be either sprayed-on or drenched in. The treatment is then washed into the thatch. Generally about 5 liters of water per $m^2$ is sufficient. Grass showing yellowing is treated by this method. In this case, the yellowed area and area surrounding the yellowed area is treated. The drench can also be applied to an apparently healthly lawn of grass to protect against severe development of disease, particularly when the Gg fungus is thought to be present in the grass.

EXAMPLES

The method of the invention is next demonstrated by the following illustrative examples.

EXAMPLE 1

Isolation of Pseudomonas strains

To 500 g of field soil was added 2.5 g of Ggt oat inoculum. The mixture was placed in a pot and 6 wheat seeds were sown. After six weeks growth, the plants were pulled up and the roots shaken to remove all but the closely adhering soil. One g of roots and adhering soil were macerated in a mortar and pestle with 1 ml of 0.01M phosphate buffer (pH 7.2). The macerate was made up to 100 ml with buffer. Serial dilutions of $1\times10^{-1}$, $1\times10^{-2}$, $1\times10^{-2}$, $1\times10^{-3}$ and $1\times10^{-4}$ were inoculated onto places of King's medium 'B', (Proteose peptone, 20 g; glycerol, 10 ml; $K_2HPO_4$, 1.5 g; $MgSO_4$, 1.5 g; agar, 15 g; $H_2O$, 1000 ml) and King's medium 'B' (KMB) amended with 45 ug/ml of novobiocin and penicillin and 75 ug/ml of cycloheximide and grown at 25° C. for 4 days. Fluorescent pseudomonads were identified by viewing the plates under ultraviolet light after 2 days of incubation at 25° C.

EXAMPLE 2

Propagation of a pure culture of individual strains of bacteria

Individual colonies from the macerated roots which developed in Example 1 were sampled with a loop and streaked onto a plate of Nutrient Broth Yeast Extract Medium (NBY) (Bacto-nutrient broth, 8 g; Bacto-yeast extract, 2 g; $K_2HPO_4$, 2 g; $KH_2PO_4$, 0.5 g; $MgSO_4.7H_2O$, 0.25 g; glucose, 5 g; agar, 15 g; $H_2O$, 1000 ml). The plate was streaked so as to generate single colonies. The plate was cultured at 25° C. for 2 days. A single colony was again selected and streaked onto a slant of NBY and used as a pure culture. Each strain was stored on a slant of NBY at 5° C., in a solution of 40 percent glycerol at −10° C. and lyophilized and stored at −10° C.

EXAMPLE 3

Greenhouse screening test using bacterial-treated seeds to suppress take-all in wheat a. Preparation of Ggt-inoculated soil. Isolates of *G. graminis* var *tritici* were started from single ascospores from the roots of diseased wheat plants. The isolates were maintained on fifth-strength potato dextrose agar (PDA) potato, 40 g; glucose, 4 g; agar, 18 g; $H_2O$, 1000 ml). To prepare inoculum, an isolate were grown for 5–7 days on PDA in petri plates and then transferred as mycelium and accompanying medium to a wide-mouth flask (1000 ml) containing autoclaved oat kernels. Two hundred fifty cc of oat kernels per jar plus 120 ml of water were autoclaved at 121° C. for 90 min on each of two consecutive days. The jars were incubated at 25° C. until the fungus had colonized the oat kernels (about 3–4 weeks). The jars were shaken once during the incubation period. After colonization, the kernels were removed from the jars, dried at room temperature, and stored in paper bags until use. The inoculum was pulverized using a Waring blendor and seived to obtain particles 0.25 to 0.5 mm in size (size C). Each of the less root disease (rating scale 0–5) than comparable untreated but diseased seedlings.

The results are tabulated in the following table:

| Treatment | Ggt[a] | Shano Silt Loam[b] (fumigated) | | | | Puget Silt Loam[b] (natural) | | | |
|---|---|---|---|---|---|---|---|---|---|
| | | Plant Height (cm) | | Root Disease | | Plant Height (cm) | | Root Disease | |
| | | .45[c] | .15[c] | .45 | .15[c] | .45[c] | .15[c] | .45[c] | .15[c] |
| Strain NRRL B-15132 | + | 12.3 a[d] | 14.0 a | 1.8 a | 1.3 a | 15.0 a | 14.6 a | 1.2 a | 1.0 a |
| Control | + | 12.2 a | 13.5 a | 2.3 b | 2.0 b | 12.8 b | 12.9 b | 1.8 b | 1.5 b |
| Strain NRRL B-15134 | + | 13.5 a | 15.0 a | 1.9 a | 1.2 a | 14.6 a | 15.8 a | 1.2 a | 1.0 a |
| Control | + | 12.2 a | 13.5 a | 2.3 b | 2.3 b | 12.8 b | 12.9 b | 1.8 b | 1.5 b |
| Strain NRRL B-15133 | + | 12.4 a | 12.6 a | 1.7 a | 1.2 a | 14.7 a | 15.4 a | 1.2 a | 1.1 a |
| Control | + | 11.9 a | 13.0 a | 3.7 b | 3.2 b | 12.8 a | 13.8 a | 2.3 b | 2.1 b |
| Strain NRRL B-15135 | + | 12.2 a | 13.7 a | 1.9 a | 1.2 a | 14.9 a | 13.8 a | 1.0 a | 0.6 a |
| Control | + | 11.9 a | 13.0 a | 3.7 b | 3.2 b | 12.8 a | 13.8 a | 2.3 b | 2.1 b |

[a]Ggt = *Gaeumannomyces graminis* var. *tritici* colonized oat kernels
[b]Shano Silt Loam was fumigated with methyl bromide
[c]Percentage (w/w) oat kernel inoculum (Particle size C, 0.25–0.50 mm) added into the soil.
[d]Means in the same column followed by the same letter are not significantly different using the Student's 't' test, $P = 0.05$.

inoculums was intimately mixed with field soil (fumigated Shano loam or non-fumigated Puget silt loan) at two concentration levels—0.45 percent and 0.15 percent inoculum per total weight of soil.

b. Preparation of bacterial-treated seeds. Wheat seeds were surfaced sterilized by immersing in a 2.6 percent solution of sodium hypochlorite for 3 minutes following by a 3-minute rinse under a continuous stream of sterile, distilled water and drying overnight under an air stream. Strains NRRL B-15132, NRRL B-15133, NRRL B-15134 and NRRL B-15135, prepared according to Examples 1 and 2, were treated as follows: each strain was individually scraped from the plates with a glass rod into a suspension of 1.0 percent methylcellulose, and thoroughly mixed with wheat seeds (four plates of bacteria per 25 ml methylcellulose solution per 50 g of seed). Coated seeds were distributed as a thin layer into petri plates, dried overnight under an airstream and separated prior to planting. Seeds contained $1 \times 10^7$ to $2 \times 10^8$ bacteria per seed.

c. Greenhouse test using bacterial-treated seeds. Each test bacterial strain and control (seed treated identically to the bacterial-treated seed except that only methylcellulose was added) was treated as follows:

Fifteen-cm-long plastic conical-shaped tubes (cones) were filled about half-full with vermiculite followed by 5 g of Ggt-inoculated soil prepared as described above which contained 0.15 or 0.45 percent (w/w) of size C inoculum. Two seeds treated as described above were placed on the soil and a 2-cm thick topping of vermiculite placed on top. Ten ml of water was added. The cones were incubated at 15°–18° C. for 4 weeks using a dark/light cycle of 12 hours. Ten cones were used for each test strain and control. After incubation, seedlings were removed from the soil, washed with water and evaluated on the basis of height and the size and number of root lesions using the following criteria: The plants were measured from the base of the stem to the top of the largest leaf. Root disease was rated on a 0–5 scale: 0=no disease, 1=one or two lesions on the roots of a given plant, 2=50–100 percent of the roots of the plant with one or more lesions each, 3=all roots of the plant with lesions and some evidence of infection on the stem, 4=lesions abundant and beginning to coalesce on the stem, and 5=plant dead or nearly so. In order for the bacterial strain to be considered suppressive to take-all, the seedlings treated with the bacteria must have averaged at least 0.3 cm taller or averaged at least 0.5 units

EXAMPLE 4

Greenhouse screening of bacteria using bacterial-treated soil to suppress take-all in wheat Pseudomonas strains NRRL B-15132 and NRRL B-15134 were isolated and propagated as described in Examples 1 and 2. The bacteria were suspended in 1.5 percent methylcellulose. Soil (Ritzville silt loam, fumigated) was amended with Ggt oat inoculum (size C and size B (0.5 to 1 mm) at a concentration level of 0.45 percent per total weight of soil) as described in Example 3. Controls consisted of soil with methylcellulose (control) and soil with methycellulose plus Ggt inoculum (Control+Ggt). Cones were prepared and planted as described in Example 3. Each cone contained $5 \times 10^6$ bacteria per gram of soil. Two wheat seeds were plated per cone. Plants were measured four weeks after planting. The results are tabulated below:

Suppression of take-all by bacteria added to the soil

| Treatment | Plant Height, cm |
|---|---|
| Strain NRRL B-15132 | 21.7 B[a] |
| Strains NRRL B-15132 + NRRL B-15134[b] | 21.0 B |
| Strain NRRL B-15134 | 18.6 C |
| Control + Ggt | 15.5 D |
| Control | 26.9 A |

[a]Means in the same column followed by the same letter are not significantly different using the least significant difference, $P = 0.05$.
[b]equal amounts.

EXAMPLE 5

Field screening test of bacteria to suppress take-all in wheat

Pseudomonas strain NRRL B-15132, NRRL B-15132 combined with NRRL B-15134, and two controls, one with Ggt-oat inoculum added to the furrow (Control & Ggt) and one without Ggt added to furrow (Control) were field tested in Mount Vernon, Washington as follows:

Three 3-meter rows for each treatment were laid out in a Latin square design. The test strain was within three meters of each control. Strains B-15132 and NRRL B-15134 were isolated and propagated as in Examples 1 and 2, respectively.

Bacteria in a one percent suspension of methylcellulose was applied to Fielder wheat seed as detailed in Example 3b. Non-bacterized seed received treatment with methylcellulose only. Ggt oat inoculum (as whole oat kernels) was prepared according to Example 3a except that it was not pulverized or seived.

Seed furrows were opened to a 10-cm depth. To the bacterial treatment and control+Ggt treatment rows were added Ggt oat-kernel inoculum at a rate of 5 g per 3-meter row. 7.5 g of bacterial-treated seed were sown per 3-meter row. Control seed (7.5 g per 3-meter row) was sown in furrows without oat inoculum. Fifty-five days after planting, plants were measured from the soil surface to the tip of the longest leaf. Measurements were made on two rows per treatment replication. Wheat heads were counted after 83 days after planting. The data is tabulated below:

| Treatment | Plant Height, cm | Number of Heads |
|---|---|---|
| Strain NRRL B-15132 | 54 B$^a$ | 258 B$^a$ |
| Control + Ggt | 50 C | 215 C |
| Control | 68 A | 452 A |
| Strains NRRL B-15132 & B-15134$^b$ | 52 B$^a$ | 257 B$^a$ |
| Control & Ggt | 50 C | 209 C |
| Control | 68 A | 452 A |

$^a$Means followed by the same letter are not significantly different, P = 0.05, according to the least significant difference.
$^b$equal amounts.

EXAMPLE 6

Use of strain NRRL B-15132 to suppress take-all in a commercial wheat field

Pseudomonas strain NRRL B-15132 was isolated and propagated as described in Examples 1 and 2. Bacteria in a suspension of 1 percent methylcellulose was applied to Daws wheat seed as described in Example 3b. The control consisted of wheat seed treated with methylcellulose only.

The commercial field used had been cropped to wheat under pivot irrigation the three previous years and was naturally infested with take-all. In the fourth yeasr, bacterial-treated and control seed were each drilled into a 6-row, 300-foot long section selected due to high incidence of take-all in the previous years. Paired plots of treated and untreated wheat were compared to give a statistical comparison. Treatment resulted in a 21 percent increase in yield. The data is tabulated in the following table:

| Treatment | Bushels/Acre |
|---|---|
| Strain NRRL B-15132 | 109 B$^a$ |
| Control | 90 A |

$^a$Means followed by the same letter are not significantly different, P = 0.05.

EXAMPLE 7

Greenhouse screening test using a bacterial drench to control Gga in turf grass a. Preparation of Gga inoculated soil. Gga oat kernel inoculum is prepared as described in Example 3a. The inoculum is pulverized using a Waring blendor and seived to obtain particles 0.25 to 0.5 mm in size (size C) and 0.5 to 1 mm in size (size B). Each of the inoculums is mixed with field soil, (fumigated Shano silt loam or non-fumigated Puget silt loam) at two concentrations 3 percent and 1 percent per total weight of soil.

b. Preparation of the turf-grass drench. Bacteria of strains NRRL B-15132, NRRL B-15133, NRRL B-15134 and NRRL B-15135, prepared according to Example 2 are scraped from the plates with a glass rod into individual suspensions of 1.5 percent methylcellulose and the suspensions are thoroughly mixed. Each suspension is adjusted to a concentration of $1 \times 10^7$ to $1 \times 10^9$ bacteria per ml and used as a soil drench.

c. Greenhouse test using a turf-grass drench. The cones are prepared as previously described in Example 3c with the following exceptions: The 5 g of Gga inoculated soil contains 1.0 percent and 3.0 percent (w/w) of inoculum of B size or C size. A 1 cm diameter plug of bent grass is added to each cone. Vermiculite is added up to the edge of the top of the plug. Two ml of the bacterial suspension (turf grass drench) is added, followed by 8 ml of water. The cones are incubated at 15°–18° C. for 8 weeks with a dark/light cycle of 12 hr. Ten cones are used for each test bacterial strains and the controls. After incubation the grass is removed, washed with water and evaluated on the basis of dry weight of the roots and leaves. In order for the bacteria to be considered suppressive to Gga, the grass treated with the bacteria must have an average of 5 percent greater root or foliage dry weight than comparable untreated but diseased grass.

EXAMPLE 8

Field screening test of bacteria to suppress Ophiobolus patch in turf grass

Pseudomonas strains NRRL B-15132 and NRRL B-15133 are field tested as follows: A 7 m by 7 m lawn of bent grass is inoculated with Gga by removing the grass as sod and adding oat grain inoculum (pulverized, mixed sizes) onto the surface of the soil. Approximately 10 g of inoculum is added to each square meter of soil. After inoculation, the grass is resodded. Each m$^2$ area constitutes a single treatment. The bacteria drench is prepared as detailed in Example 7b. Non-treated grass receives a drench of only methylcellulose. The bacterial drench is added at 1 liter per 1 m$^2$ followed by 5 liters of water. Each treatment is rated on the basis of the area of yellowed grass or dry weight. To be considered suppressive to Gga, the treated grass must average at least 5 percent less yellowed area or the average at least 5 percent greater root or foliage dry weight.

EXAMPLE 9

Use of Strains NRRL B-15132 and NRRL B-15133 to control Ophiobolus patch in the field The bacterial drench prepared as previously described is added to an established golf putting green of bent grass that is showing symptoms of the disease Ophiobolus patch. The bacterial drench is applied using a Hudson Knapsak sprayer at the first appearance of yellowing of the grass. The treatment rate is about 1 liter of drench per m$^2$ of lawn. The yellowed area is treated and the area 1 meter in diameter around the yellowed spat is also treated. After treatment the golf green is irrigated for 1 hour.

It is understood that the foregoing detailed description is given merely by way of illustration and that modification and variations may be made within, without departing from the spirit and scope of the invention.

Having thus described our invention, we claim:

1. A method for screening bacteria for selection of strains which will suppress under field conditions diseases caused by the fungus *Gaeumannomyces graminis* (Gg), which comprises:

(a) isolating strains of potentially-suppressive bacteria from roots of plants of the variety to be protected grown in soil containing added Gg inoculum;

(b) screening strains isolated in the previous step for suppression of disease-causing Gg fungus in the greenhouse as follows:

(1) if the plants to be protected are cereal crops, growing the plants in the greenhouse in the presence of bacteria in a concentration of about $1 \times 10^7$ to $2 \times 10^8$ bacteria per seed or about $1 \times 10^6$ to $1 \times 10^7$ bacteria per gram of soil and in the presence of Gg inoculum having a concentration and particle size which optimizes the selection of field-effective strains and minimizes the selection of field-ineffective strains; or if the plants to be protected are turf grass, growing the grass in the greenhouse in the presence of bacteria in a concentration of about $2 \times 10^7$ to $2 \times 10^9$ bacteria per 1-cm diameter of grass and in the presence of Gg inoculum having a concentration and particle size which optimizes the selection of field-effective strains and minimizes the selection of field-ineffective strains;

(2) growing plants of the variety to be protected as in step (b)(1), without the addition of bacteria; and (3) selecting as greenhouse-suppressive bacteria those strains which suppressed Gg fungus as follows:
if the bacterial-treated plants are cereal crops, the bacteria must suppress Gg fungus such that the bacterial-treated plants average at least 0.3 cm taller or at least 0.5 units less root disease than plants grown without added bacteria, or if the bacterial-treated plants are turf grass, the bacteria must suppress Gg fungus such that the bacterial-treated grass averages at least 5 percent more root or foliage dry weight than grass grown without added bacteria; and (c) screening the so-selected bacteria of step (b)(3) for suppression of disease-causing Gg fungus in the field as follows:

(1) if the plants to be protected are cereal crops, growing the plants in the field in the presence of the so-selected strain of bacteria of step (b)(3) in a concentration of about $1'10^7$ to $2 \times 10^8$ bacteria per seed and in the presence of Gg inoculum in a concentration which optimizes the selection of field-effective strains and minimizes the selection of field-ineffective strains; or if the plants to be protected are turf grass, growing the grass in the presence of the so-selected strain of bacteria of step (b)(3) in a concentration of about $1 \times 10^{10}$ to $1 \times 10^{12}$ bacteria per square meter of grass and in the presence of Gg inoculum in a concentration which optimizes the selection of field-effective strains and minimizes the selection of field-ineffective strains;

(2) growing in the field plants of the variety to be protected as in step (c)(1) without the addition of bacteria; and (3) selecting as field-suppressive bacteria those strains which suppressed Gg fungus as follows:
if the bacterial-treated plants are cereal crops, the bacteria must suppress Gg fungus such that the crops are 1.0 cm taller or grow 5 percent more heads or have 0.1 units less root disease than plants grown without added bacteria, or if the bacterial-treated plants are turf grass, the bacteria must suppress Gg fungus such than the bacterial-treated grass averages at least 5 percent less yellowed area or averages at least 5 percent more root or foliage dry weight than grass grown without added bacteria.

2. The method of claim 1 wherein the particle size of the inoculum in the greenhouse screening of step b is about 0.25 to 1 mm and wherein the concentration of inoculum in the greenhouse screening is about 0.05 to 1.0 percent per total weight of soil where the plants to be protected are cereal crops or about 0.5 to 4.0 percent per total weight of soil where the plants to be pertected are turf grass; and where the concentration of inoculum in the field screening of step c is about 4 to 5 grams per 3-meter row where the plants to be protected are cereal crops or about 9 to 11 grams per square meter patch where the plants to be protected are turf grass.

3. The method of claim 2 wherein the concentration of inoculum in the greenhouse screening of step b is about 0.15 to to 0.45 percent inoculum per total weight of soil where the plants to be protected are cereal crops or about 1 to 3 percent inoculum per total weight of soil where the plants to be protected are turf grass.

4. The method of claim 1, further comprising:
(d) applying bacteria of the strain selected in the previous step to seeds of plants of the variety to be protected in a concentration of about $1 \times 10^7$ to $2 \times 10^8$ bacteria per seed.

5. The method of claim 1, further comprising preparing bacterial treatment solution having a concentration of about $1 \times 10^7$ to $1 \times 10^9$ bacteria of the strain selected in the previous step per ml of solution.

6. The method of claim 1 wherein the plant to be protected is wheat and the disease-causing Gg fungus is *Gaeumannomyces graminis* var *tritici*.

7. The method of claim 1 wherein the plant to be protected is turf grass and the disease-causing Gg fungus is *Gaeumannomyces graminis* var *avenae*.

8. The method of claim 1 wherein the plant to be protected is turf grass and the disease-causing Gg fungus is *Gaeumannomyces graminis* var *graminis*.

9. A product produced in accordance with the method of claim 4.

10. A product produced in accordance with the method of claim 5.

11. A method of controlling disease-causing Gg fungus in the field, which comprises:
(a) isolating strains of potentially-suppressive bacteria from roots of plants of the variety to be protected grown in soil containing added Gg inoculum;
(b) screening the strains isolated in the previous step for suppression of disease-causing Gg fungus in the greenhouse as follows:
(1) if the plants to be protected are cereal crops, growing the plants in the greenhouse in the presence of bacteria in a concentration of about $1 \times 10^7$ to $2 \times 10^8$ bacteria per seed or about $1 \times 10^6$ to $1 \times 10^7$ bacteria per gram of soil and in the presence of Gg inoculum having a concentration of 0.05 to 1.0 percent inoculum per weight of soil and a particle size of about 0.25 to 1 mm; or if the plants to be protected are turf grass, growing the grass in the greenhouse in the presence of bacteria in a concentration of about $2 \times 10^7$ to $2 \times 10^9$ bacteria per 1-cm diameter of grass and in the presence of Gg inoculum having a concentration of about 0.5 to 4 percent per total weight of soil and a particle size of about 0.25 to 1 mm;

(2) growing plants of the variety to be protected as in step (b)(1), without the addition of bacteria; and (3) selecting as suppressive bacteria those strains which suppress Gg fungus as follows:

if the bacteria-treated plants are cereal crops, the bacteria must suppress Gg fungus such that the bacterial-treated plants average at least 0.3 cm taller or at least 0.5 units less root disease than plants grown without added bacteria, or if the bacterial-treated plants are turf grass, the bacteria must suppress Gg fungus such that the bacterial-treated grass averages at least 5 percent more root or foliage dry weight than grass grown without added bacteria; and (c) screening the so-selected bacteria of step (b)(3) for suppression of disease causing Gg fungus in the field as follows:

(1) if the plants to be protected are cereal crops, growing the plants in the field in the presence of the so-selected strain of bacteria of step (b)(3) in a concentration of about $1 \times 10^7$ to $2 \times 10^8$ bacteria per seed and in the presence of Gg inoculum in a concentration of about 4 to 5 grams per 3-meter row; or if the plants to be protected are turf grass, growing the grass in the presence of the so-selected strain of bacteria of step (b)(3) in a concentration of about $1 \times 10^{10}$ to $1 \times 10^{12}$ bacteria per square meter of grass and in the presence of Gg inoculum in a concentration of about 9 to 11 grams of inoculum per square meter of grass;

(2) growing in the field plants of the variety to be protected as in step (c)(1) without the addition of bacteria; and (3) selecting as field-suppressive bacteria those strains which suppress Gg fungus as follows: if the bacterial-treated plants are cereal crops, the bacteria must suppress Gg fungus such that the crops are 1 cm taller or grow 5 percent more heads or have 0.1 units less root disease than plants grown without added bacteria, or if the bacterial-treated plants are turf grass, the bacteria must suppress Gg fungus such that the bacterial-treated grass averages at least 5 percent less yellowed area or averages at least 5 percent more root or foliage dry weight than grass grown without added bacteria; and (d) growing in the field plants to be protected in the presence of a suppressive amount of the bacteria selected in the previous step.

12. The method of claim 11 wherein said seeds of the plant to be protected in the field in step d are treated with a concentration of of about $1 \times 10^7$ to $2 \times 10^8$ bacteria per seed of field-suppressive bacteria before planting in the field.

13. The method of claim 12 wherein the plant to be protected is wheat and the disease-causing Gg fungus *Gaeumannomyces graminis* var *tritici.*

14. The method of claim 11 wherein plants of the variety to be protected in the field in step d are treated with a bacterial treatment solution containing about $1 \times 10^7$ to $1 \times 10^9$ bacteria per ml of solution.

15. The method of claim 14 wherein the plant to be protected is turf grass and the disease-causing Gg fungus is *Gaeumannomyces graminis* var *avenae.*

16. The method of claim 14 wherein the plant to be protected is turf grass and the disease-causing Gg fungus is *Gaeumannomyces graminis* var *graminis.*

17. A method of controlling disease-causing *Gaeumannomyces graminis* fungus (Gg) in field-grown cereal crops, which comprises treating cereal seed with a biologically pure culture of bacteria which suppresses diseases caused by Gg under field conditions as determined by passing the screen test of claim 1, the concentration of bacteria per seed of said treatment being about $1 \times 10^7$ to $2 \times 10^8$ bacteria per seed.

18. A method of controlling disease-causing *Gaeumannomyces graminis* fungus (Gg) in turf grass, which comprises treating the grass with a bacterial treatment solution containing a biologically pure culture of bacteria which suppresses Gg under field conditions as determined by passing the screen test of claim 1, said treatment solution having a concentration of about $1 \times 10^7$ to $1 \times 10^9$ bacteria per ml of solution.

19. The method of claim 18, further comprising watering said treatment solution into the crown area of the grass.

20. The method of claim 19 wherein said bacterial treatment solution is applied in a concentration of about 1 liter per square meter of grass.

21. The method of claim 17 or 18 wherein said biologically pure culture of bacteria comprises one or more strains of Gg-suppressive *Pseudomonas fluorescens.*

22. The method of claim 21 wherein said *Pseudomonas fluorescens* bacteria are selected from the group consisting of NRRL B-15132, NRRL B-15133, NRRL B-15134 and NRRL B-15135.

23. A biologically pure culture of bacteria which suppresses diseases caused by the fungus *Gaeumannomyces graminis* (Gg) under field conditions as determined by passing the screen test of claim 1.

24. The biological pure culture of claim 23 wherein said bacteria comprises one or more strains of *Pseudomonas fluorescens.*

25. The biologically pure culture of claim 24 wherein said *Pseudomonas fluorescens* bacteria is selected from the group consisting of NRRL B-15132, NRRL B-15133, NRRL B-15134 and NRRL B-15135.

* * * * *

UNITED STATES PATENT AND TRADEMARK OFFICE
CERTIFICATE OF CORRECTION

PATENT NO. : 4,456,684
DATED : June 26, 1984
INVENTOR(S) : David M. Weller et al.

It is certified that error appears in the above—identified patent and that said Letters Patent is hereby corrected as shown below:

In column 2, line 14, delete "dealy" and insert -- delay --.

In column 2, line 28, delete "successively" and insert -- successive --.

In column 7, line 50, delete "procedures" and insert -- procedure --.

In column 7, line 64, delete "growth" and insert -- grown --.

In column 10, line 24, delete "places" and insert -- plates --.

In column 10, line 58, delete "were" and insert -- was --.

In column 11, line 22, after the word "Shano", insert -- silt --.

In column 15, line 49, delete "1'10$^7$" and insert -- 1X10$^7$ --.

Signed and Sealed this

Twenty-third Day of April 1985

[SEAL]

Attest:

DONALD J. QUIGG

*Attesting Officer*  *Acting Commissioner of Patents and Trademarks*